(12) United States Patent
Osorio

(10) Patent No.: US 8,944,052 B2
(45) Date of Patent: Feb. 3, 2015

(54) APPARATUS AND METHODS FOR DELIVERY OF THERAPEUTIC AGENTS TO MUCOUS OR SEROUS MEMBRANE

(76) Inventor: Ivan Osorio, Leawood, KS (US)

(*) Notice: Subject to any disclaimer, the term of this patent is extended or adjusted under 35 U.S.C. 154(b) by 596 days.

(21) Appl. No.: 13/116,782

(22) Filed: May 26, 2011

(65) Prior Publication Data

US 2012/0298105 A1 Nov. 29, 2012

(51) Int. Cl.

| | | |
|---|---|---|
| A61M 11/00 | (2006.01) |
| A61N 1/36 | (2006.01) |
| A61N 1/05 | (2006.01) |
| A61M 15/08 | (2006.01) |
| A61M 19/00 | (2006.01) |
| A61M 21/00 | (2006.01) |
| A61M 15/00 | (2006.01) |
| A61B 5/0402 | (2006.01) |
| A61B 5/053 | (2006.01) |
| A61M 21/02 | (2006.01) |

(52) U.S. Cl.
CPC ............ *A61N 1/3605* (2013.01); *A61N 1/0546* (2013.01); *A61N 1/0548* (2013.01); *A61M 15/08* (2013.01); *A61M 19/00* (2013.01); *A61M 21/00* (2013.01); *A61M 15/0003* (2013.01); *A61M 15/0066* (2013.01); *A61M 15/085* (2013.01); *A61B 5/0402* (2013.01); *A61B 5/0531* (2013.01); *A61M 11/00* (2013.01); *A61M 21/02* (2013.01); *A61M 2021/0066* (2013.01); *A61M 2021/0072* (2013.01); *A61M 2202/0413* (2013.01); *A61M 2202/0466* (2013.01); *A61M 2202/0496* (2013.01); *A61M 2205/3375* (2013.01); *A61M 2205/3523* (2013.01); *A61M 2205/3561* (2013.01); *A61M 2205/3592* (2013.01); *A61M 2205/52* (2013.01); *A61M 2205/8206* (2013.01); *A61M 2230/04* (2013.01); *A61M 2230/10* (2013.01); *A61M 2230/20* (2013.01); *A61M 2230/201* (2013.01); *A61M 2230/205* (2013.01); *A61M 2230/30* (2013.01); *A61M 2230/40* (2013.01); *A61M 2230/42* (2013.01); *A61M 2230/432* (2013.01); *A61M 2230/50* (2013.01); *A61M 2230/60* (2013.01); *A61M 2230/62* (2013.01); *A61M 2230/63* (2013.01); *A61M 2230/65* (2013.01)
USPC ............ 128/203.14; 128/204.21; 128/204.23

(58) Field of Classification Search
USPC ............ 128/204.23, 203.14, 204.18, 204.21, 128/203.12, 200.24
See application file for complete search history.

(56) References Cited

U.S. PATENT DOCUMENTS

| | | | |
|---|---|---|---|
| 6,715,485 B1 * | 4/2004 | Djupesland | 128/203.15 |
| 2010/0078015 A1 * | 4/2010 | Imran | 128/200.23 |
| 2013/0276785 A1 * | 10/2013 | Melker et al. | 128/204.23 |

* cited by examiner

*Primary Examiner* — Steven Douglas
(74) *Attorney, Agent, or Firm* — Kutak Rock LLP; Marcellus A. Chase

(57) ABSTRACT

A method, apparatus, and system are provided for mucous membrane therapy. The method includes receiving at least one body signal from a patient; detecting a condition of the patient based on the body signal; and administering the therapy to at least one of a mucous membrane or a serous membrane of the patient. A medical device system configured to implement the method is provided. A computer-readable storage device for storing instructions that, when executed by a processor, perform the method is also provided.

8 Claims, 10 Drawing Sheets

APPARATUS AND METHODS FOR DELIVERY OF THERAPEUTIC AGENTS TO MUCOUS OR SEROUS MEMBRANE

BACKGROUND

1. Field of the Disclosure

The present disclosure relates generally to the fields of automated detection and treatment of medical conditions, and more specifically, to treatment of medical conditions based upon automated detection and delivery of therapy via mucous or serous membranes.

2. Description of Related Art

A metered-dose inhaler may be used to deliver a specific amount of medication to the lungs to treat asthma, chronic obstructive pulmonary disease (COPD), and other respiratory diseases. For a metered-dose inhaler to be effective, typically, a patient suffering such a disease must recognize that he or she is in a situation where use of the inhaler is appropriate, and he or she must bring the inhaler to the mouth and activate it.

A patient's failure to appropriately activate the metered-dose inhaler may reduce the effectiveness of the treatment and may fail to capitalize on the opportunity to intervene even before the first symptom occurs, to the detriment of the patient. Moreover, leaving the determination of timing and dosage of delivery of medicine to the patient may have further disadvantages. For example, the patient may not be in a position to decide on the appropriate timing for delivery of therapy. Further, errors in the dosage of the medication may occur. Still further, relying on the patient to deliver medication can lead to incorrect application of therapy, thereby possibly reducing efficacy, causing an overdose, and/or leading to addiction in the case of certain analgesics or CNS acting drugs. Also, metered-dose inhalers are generally only used against respiratory diseases.

SUMMARY OF THE DISCLOSURE

In one embodiment, the present disclosure relates to a method, comprising receiving at least one body signal from a patient; detecting a condition of the patient based on the body signal; and administering the therapy to at least one of a mucous membrane or a serous membrane of the patient, in response to the determining.

In another embodiment, the present disclosure relates to a medical device system comprising at least one sensor configured to sense at least one body signal from a patient; a detection unit configured to receive at least one body signal from the sensor and detect a condition based on at least the body signal; and a therapy device configured to administer the therapy to at least one of a mucous membrane or a serous membrane of the patient.

In an additional embodiment, the present disclosure relates to a computer-readable storage device for storing instructions that, when executed by a processor, perform a method as described above.

In one aspect of any of the foregoing embodiments, the condition may be an epileptic seizure.

BRIEF DESCRIPTION OF THE DRAWINGS

The disclosure may be understood by reference to the following description taken in conjunction with the accompanying drawings, in which like reference numerals identify like elements, and in which.

Figure 1A:
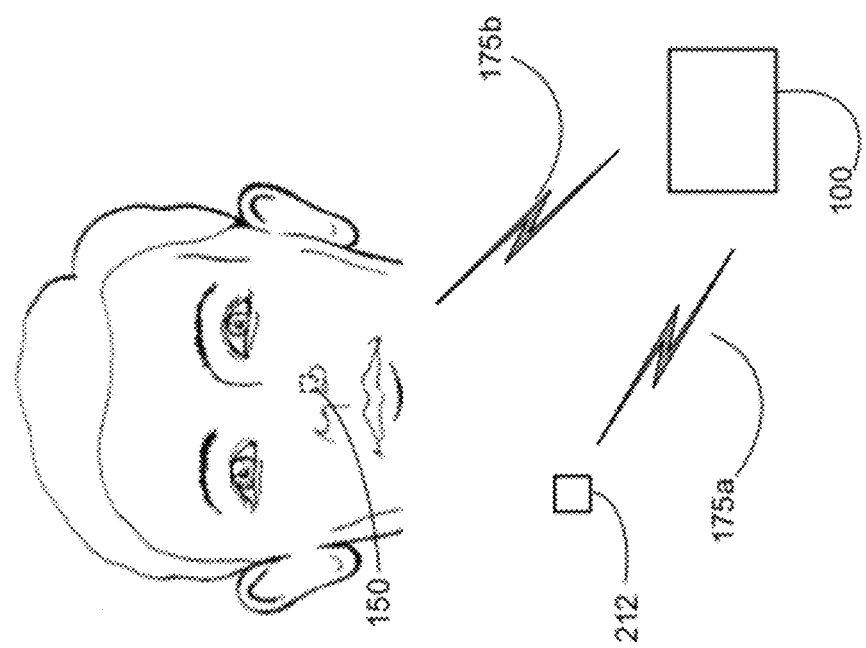
FIG. 1A provides a stylized diagram of a medical device system comprising a device, a sensor, and a delivery device configured to deliver a therapy to a mucous membrane of the nose, in accordance with one illustrative embodiment of the present disclosure.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the appended claims.

DESCRIPTION OF ILLUSTRATIVE EMBODIMENTS

Illustrative embodiments of the disclosure are described herein. Not all features of an actual implementation are described. In the development of any actual embodiment, numerous implementation-specific decisions must be made to achieve the design-specific goals, which will vary from one implementation to another. While possibly complex and time-consuming, such a development effort would nevertheless be a routine undertaking for persons of ordinary skill in the art having the benefit of this disclosure.

This document does not intend to distinguish between components that differ in name but not function. The terms "including" and "includes" are used in an open-ended fashion, and should be interpreted to mean "including, but not limited to." "Couple" or "couples" is intended to mean either a direct or an indirect electrical connection. "Direct contact," "direct attachment," or providing a "direct coupling" indicates that a surface of a first element contacts the surface of a second element with no substantial attenuating medium there between, but are not intended to exclude the presence of small quantities of substances, such as bodily fluids, that do not substantially attenuate electrical connections. The word "or" is used in the inclusive sense (i.e., "and/or") unless a specific use to the contrary is explicitly stated.

"Electrode" or "electrodes" may refer to one or more stimulation electrodes (i.e., electrodes for delivering a therapeutic signal generated by an IMD to a tissue), sensing electrodes (i.e., electrodes for sensing a physiological indication of a state of a patient's body), and/or electrodes that are capable of both signal sensing and therapy delivery.

In one embodiment, the present disclosure relates to a method comprising receiving at least one body signal from a patient; detecting a condition of the patient based on the body signal; and administering a therapy to at least one of a mucous membrane or a serous membrane of the patient, in response to the detecting.

Any one or more of numerous body signals may be received from a patient. A "signal" herein refers to a signal generated by any body source and received by a sensor.

Exemplary body signals include, but are not limited to, autonomic signals (e.g., cardiac activity, respiratory activity, electrodermal activity, brain waves, cephalic vasomotor response, hand surface or scalp temperature); neurologic signals (e.g., body movement, frontalis, forearm or neck EMG, responsiveness, awareness); endocrine signals (e.g. cortisol concentrations); metabolic signals (e.g., blood glucose levels); tissue stress makers (e.g., salivary amylase, lactic acid, troponin, free radicals); and signals indicative of the concentration of a medication or chemical (e.g., electrolyte) in a body fluid (e.g., blood, saliva, urine). Further, said signal may be in form of electroencephalography (EEG) or electrocorticography (ECoG), electrocardiography (EKG) signals, electromyography (EMG) signals, thermography, sound, ultrasound, or plethysmography in any of its forms.

More information regarding exemplary body signals can be found in U.S. patent application Ser. No. 13/040,996, filed Mar. 4, 2011 and U.S. patent application Ser. No. 13/091,033, filed Apr. 20, 2011, which are incorporated herein by reference in its entirety. As will be apparent to the skilled artisan, some of the body signals listed herein and in the applications incorporated by reference as belonging to a particular signal category may, at extreme values or under abnormal body conditions, be informative about other signal categories. For example, blood pH is generally a metabolic signal, but at very high values, can be considered a tissue stress marker.

Particular cardiac signal features that may be used include, but are not limited to, T-wave amplitude, QT variability index, low- and high-frequency heart rate variability, approximate entropy of R—R intervals, approximate entropy of QT intervals or their ratio (ApEnQT/ApEnRR), stroke volume, pre-ejection period, left-ventricular ejection time, Heather index, blood pressure, pulse amplitude, and transit time. Respiratory signal features include but are not limited to tidal volume and its variability, inspiratory flow rate, the ratio of the inspiratory over the expiratory slope, duty cycle, and end-tidal $pCO_2$. Other useful autonomic signals are the cardiovascular reflex as tested using Ewing's battery, frontal sympathetic skin responses, the trigemino-parasympathetic reflex as measured by the vasodilator response of forehead skin bilaterally using photoplethysmography, the somato-sympathetic reflex by vasoconstriction in the index finger measured using for example changes in temperature; cephalic vasomotor response; hand surface temperature; and heart rate and skin resistance level.

Skin conductance is another autonomic signal. In one embodiment, the tonic or phasic components of skin conductance and its multiple possible mathematical transformations such as its mean level, the derivate of the mean, its number of fluctuations/unit time which expresses sympathetic skin nerve activity, or the amplitude of the fluctuations will be measured with (exosomatic) or without (endosomatic) resorting to the use of electrical (DC or AC) currents. Skin potential (response or level) or skin resistance may also be measured. In this disclosure the terms electrodermal activity, skin conductance, galvanic skin response, or sympathetic skin responses are used interchangeably.

More information on body signals, such as cardiac signals, respiratory signals, body movement signals, skin resistance signals, responsiveness signals, and awareness signals, as well as techniques and devices for the acquisition thereof, is provided by U.S. patent application Ser. No. 12/896,525, filed Oct. 1, 2010, which is incorporated herein by reference in its entirety.

A signal indicative of the concentration of a medication in a body fluid can be acquired by contacting a sensor capable of quantifying a patient's concentration of the therapeutic medication or means in a body tissue or fluid sample of blood, saliva, urine, hair and/or the like from the patient. The sensor can be external to the patient's body, with samples of blood yielded by lancing, or internal to the patient's body, such that the sensing element of the sensor is in direct or indirect contact with the patient's bloodstream.

In an alternative or additional embodiment, a patient and/or a physician may make an assessment of one or more states of the patient's body, and this assessment can be considered in making a detection as discussed below. However, such an assessment is not a "signal" as used herein. Numerous conditions can be detected based on one or more body signals. "Condition" is used herein to refer to both a state of the patient having a medical condition (e.g., a patient who has had one or more epileptic seizures has the condition, epilepsy) and a particular acute manifestation of a medical event (e.g., for a patient with epilepsy, each epileptic seizure can be a detected condition). Condition may be used interchangeably with disorder or disease.

In one embodiment, the detected condition may be a neurological condition. Exemplary neurological conditions which can be detected include epilepsy (including epileptic seizures and other epileptic events), headaches (e.g., any form of migraine, cluster headache among others), facial pain, cranial nerve neuralgias (e.g., trigeminal) or movement disorders, such as Parkinson's disease (including episodes of rigidity, tremor, or dyskinesia) and psychiatric conditions (such as a panic disorder, an anxiety disorder, agitated behavior, or violent behavior). In a particular embodiment, the neurological condition is epilepsy; and the body signal is at least one of a cardiac signal, a respiration signal, a body movement signal, a skin resistance signal, a responsiveness signal, or an awareness signal. The detection of epilepsy or an epileptic event from such signals is described in U.S. patent application Ser. No. 12/770,562, filed Apr. 29, 2010, which is incorporated herein by reference in its entirety, and U.S. patent application Ser. No. 12/896,525, filed Oct. 1, 2010, which is incorporated herein by reference in its entirety.

Figure 8:
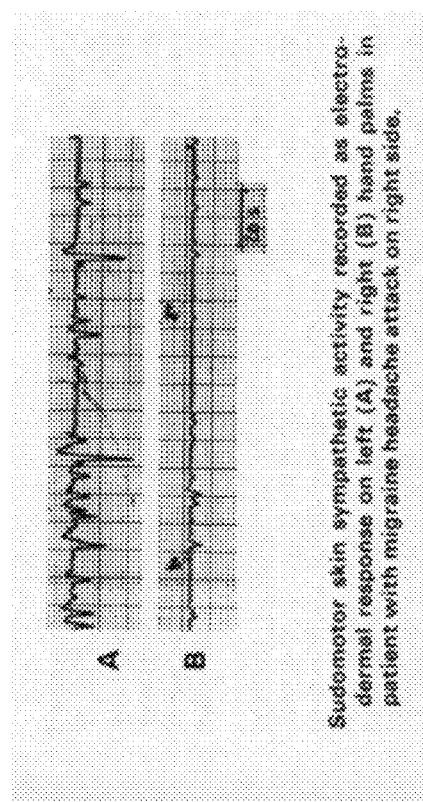
FIG. 8 shows an ipsilateral electrodermal response to migraine, in accordance with one illustrative embodiment of the present disclosure.

In yet another embodiment, the neurological condition is a movement disorder; and the body signal is a body movement signal. For example, an accelerometer mounted on a limb of a patient suffering from Parkinson's disease can give information about tremor in that limb or about rigidity and body posture In yet another embodiment, the neurological condition is migraine; and the body signal is an electrodermal activity signal. Changes in this activity are commonly observed in migraneurs during and in-between headaches. For example, a decrease in the amplitude of electrodermal responses and in the number of fluctuations/time unit has been observed on the limbs ipsilateral to the side of the pain. (FIG. 8). Electrodermal activity may be an indicator of autonomic arousal and of sympathetic nerve activity and thus may be dependent among others on pain level, level of consciousness (whether physiologic (e.g., wakefulness vs. sleep and within sleep REM vs. non-REM) or pathologic (e.g., coma), and emotional (fearful vs. calm) and cognitive states (problem solving vs. relaxing)). Electrodermal activity may be also dependent on other factors such as race, age, gender, time of day, ambient temperature, humidity and other meteorological conditions. Useful interpretation of electrodermal responses for detection of changes in body organ state or activity may be facilitated through monitoring and logging of factors that influence it and also by taking in to account the fact that this response habituates.

To optimize sensitivity, specificity and speed of detection of changes in organ state (e.g., seizures, migraine attack) a patient may be used as her/his own control in analyzing electrodermal activity. Additionally, other signals such as heart rate, respiration, responsiveness, and/or the like may be used to validate (e.g., confirm or reject) the detection. By way of example, subjective emotional experience which alters electrodermal activity, heart rate and respiration, also affects facial behavior/expression, which may be tracked and quantified with EMG signals of the corrugator supercilii and zygomaticus major muscles. Moreover, anger may be distinguished from fear as the former may be characterized by greater increases in diastolic blood pressure, greater increases in muscle tension, and greater increases in the number of skin conductance responses than the latter; in contrast, the emotion of fear (anxiety) may show greater increases in the skin conductance level (amplitude), muscle tension peaks and respiration rate than anger.

In a different embodiment, measurement of the diameter of one or more arteries (e.g., the superficial temporal) which dilates on the ipsilateral side during a migraine attack) or measurement with transcranial doppler of blood flow or local pulse pressure (e.g., in the middle cerebral artery which decreases on the affected side in the case of unilateral headache) may be used to detect the onset of a migraine attack, deliver a therapy to a mucous or serous membrane, or monitor the response and log relevant information such as time of onset or duration of the attack, among others.

Non-neurological conditions can also be detected according to techniques disclosed herein. In one embodiment, the non-neurological condition is asthma, COPD, a cardiac disorder, vasodepressive syncope, or diabetes. In a particular embodiment, the non-neurological condition is at least one of asthma or COPD; and the body signal is at least one of a blood oxygen saturation signal or a lung sounds signal. For example, an asthma attack may lead to a decrease in blood oxygen saturation, and can give rise to lung sounds colloquially referred to as "wheezing" reflective of an increase in the pitch (higher frequencies) of respiratory sounds due to bronchoconstriction; this and changes in lung sound quality, or prolongation of the expiratory phase compared to asymptomatic periods, may allow the early detection (before oxygen saturation drops or carbon dioxide rises) of an asthma attack.

In another embodiment, the condition involves the blood concentration of a therapeutic medication being below a first concentration or above a second concentration. For example, it may be desirable for a patient to maintain a certain minimum blood concentration of a medication to treat, control, or prevent an episode of a disease such as an epileptic seizure. For another example, it may be desirable for a patient to maintain the concentration below a maximum to avoid dose-related side effects.

Once the condition has been detected, or the determination of a blood concentration of a medicament or a chemical has taken place, the method can further comprise enabling at least one action such as selecting at least one intervention or therapy for the condition, raising the concentration of a medication through the administration of supplemental doses or lowering the concentration by delaying delivery of a dose until the medication's concentration is below a certain threshold.

In another embodiment, if a first drug's concentration is below a therapeutic level, a fast/faster acting formulation of the first drug or a fast acting second drug may be delivered until either the first or second drug reaches its therapeutic concentration, or a different therapy modality may be chosen, such as thermal or electrical therapy, to prevent or treat a condition.

One or more therapies may be available. In embodiments wherein a single therapy (e.g., a single medication, in a single formulation, for delivery of a single dosage via one route of administration) may be selected prior to performance of the method, upon detecting the condition, administration of the therapy can follow immediately. In embodiments wherein multiple therapies (e.g., different dosages or delivery routes of one or more drugs, and/or therapies from across pharmacological, electrical, thermal, and/or other modalities) are available, the method can further comprise determining a therapy prior to or after detecting the condition and before administering the therapy.

Generally, the therapy may be one suitable for administration to at least one of a mucous membrane or a serous membrane of the patient.

Mucous membranes (which may also be termed mucosae) are generally linings of body cavities that are generally exposed to the environment or objects from the environment that are brought into the body. Exemplary mucous membranes include, but are not limited to, the nostrils, various structures of the mouth (e.g., tongue, lips, and gums, among others), the eyelids, the ears, the lung alveoli, the stomach lining, the linings of the intestines, the glans clitoridis, the glans penis, the inside of the prepuce, the inside of the clitoral hood, the endometrium of the uterus, the urethra, and the anus, among others. Despite the name, not all mucous membranes secrete mucus. As used herein, the alveoli of the lung are mucous membranes. Embodiments of the present disclosure may be employed to use mucous membrane advantageously to cause efficient absorption of medication.

Serous membranes (which may also be termed serosa) are generally linings of body cavities that are not exposed to the environment or foreign objects under normal circumstances. Many serous membranes, but not necessarily all, secrete serous fluid. Generally, serous membranes are those recognized as reducing friction in body movement. Exemplary serous membranes include the lining of the pericardial cavity (surrounding the heart), the lining of the pleural cavity (surrounding the lungs), and the peritoneum (surrounding most abdominal organs). Various organs with these cavities may have serous membrane linings as well, e.g., the pericardium and epicardium of the heart, the perimetrium of the uterus, etc.

In one embodiment, a therapy comprises one or more doses of a medication capable of being absorbed by a mucous membrane or a serous membrane and entering the patient's bloodstream therefrom. The particular therapy can be determined from a number of possible medications that differ in active compound, inert ingredients, amount of active compound per dose, particle size and/or particle density in the case of aerosols, number of doses, rate of delivery and/or location and number of mucous or serous membranes and the area of membrane to which the medication is to be delivered. In the case of drug delivery to nasal or oral mucous membranes, particle size would determine the size of the target area. For example, if the aim is to deposit drug in the entire upper and lower respiratory tracts a heterodisperse aerosol containing drug particles ranging in size from >10 micrometers (μm) to 1 μm would be delivered through the nose, the larger (>10 μm particles) being trapped in the nose and its turbinates and the smaller particles advancing further down the bronchial tree with the smallest one (1-5 μm) reaching the alveoli. Aerosols containing only one particle size (monodisperse) may be used to target only the nose and main bronchii or mainly the alveoli. In another embodiment, a combination of two or more medications may be combined during the delivery to a mucous membrane. Particular medications, concentrations, numbers of doses, etc. suitable for treating a particular condition can generally be selected.

Exemplary medicaments include, but are not limited to, a benzodiazepine, a barbiturate, a CNS depressant drug, an anti-seizure drug, a local anesthetic, a vasoactive agent, an anti-inflammatory drug, a non-narcotic analgesic, a narcotic analgesic, a medicinal gas, or two or more thereof, a bronchodilator, an anti-inflammatory drug, or oxygen. In one embodiment, the medicament is delivered in an absorbable or inhalable form. Drugs or compounds delivered to the mucosae and serosae will not only enter the bloodstream but also diffuse to sensory and autonomic structures, thus having local and systemic effects.

In one embodiment, which may be useful when the condition is migraine, the therapy may be an anesthetic (e.g., lidocaine), an analgesic (e.g., fentanyl), an anti-inflammatory (e.g., corticosteroid), or a vaso-active agent (e.g., sumatriptan or related drugs) delivered to a mucous membrane of the nose/turbinates.

From a treatment dynamics perspective, membrane cooling may be substantially equivalent to using a local anesthetic.

In one embodiment, the therapy is a medication in an aerosol formulation, a gas formulation, a liquid formulation, a controlled release gel formulation. Such formulations may be especially capable of being absorbed by a mucous membrane or a serous membrane.

In one embodiment, the therapy is delivery of a dosage of a therapeutic medication sufficient to raise the blood concentration of the therapeutic medication above a first concentration.

Upon determination of the therapy, the method can further comprise administering the therapy to at least one of a mucous membrane or a serous membrane of the patient, in response to the determining.

The particular mucous membrane or serous membrane can generally be selected. In one embodiment, the mucous membrane or serous membrane may be a nasal mucous membrane or a lung/alveoli mucous membrane. Nasal passages may allow relatively rapid absorption of the therapy to the bloodstream, and the lung has a large area and the blood vessels in proximity thereto are near the heart. Moreover, the proximity of the nasal passages to the brain and to autonomic structures may be used advantageously to more efficiently treat neurological conditions, e.g., migraine, headaches, or epilepsy.

Administering may be performed using any appropriate technique. In one embodiment, a medication may be stored in a reservoir, and a dose of the medication may be delivered by a pump in fluid communication with the reservoir that may be automatically triggered by the detection of an onset of an episode, or by a patient, or a caregiver.

A plurality of therapies, as defined herein, can be administered. In one embodiment, the plurality of therapies may comprise delivery of a plurality of drugs to the mucous and/or serous membrane(s) in response to the detection of the condition.

In a further embodiment, additional therapies can be delivered to the patient's body or portions thereof. For example, in one embodiment, the method further comprises delivering a therapy to a cranial nerve of the patient, said therapy being electrical, thermal or pharmacologic. Exemplary cranial nerves include, but are not limited to, a trigeminal nerve, a glossopharyngeal nerve, a hypoglossal nerve, a vagus nerve, and an olfactory nerve, among others. In one embodiment, therapy may be delivered to phrenic and/or intercostals nerves or to their origins.

Also, a method according to the present disclosure may further comprise logging one or more of the condition detected (e.g., an epileptic seizure), the date and time of detection, the severity (e.g., duration, intensity) of the condition, the type(s) of therapy(ies) delivered, the site(s) of delivery of the therapy(ies), the dose of the therapy(ies), the level of efficacy of the therapy(ies), the level of tolerance of the therapy(ies), and the presence or absence of adverse effects of the therapy(ies).

In an additional embodiment, the present disclosure relates to a computer-readable storage device for storing instructions that, when executed by a processor, perform a method as described above.

In another embodiment, the present disclosure relates to a medical device system, comprising at least one sensor configured to sense at least one body signal from a patient; a detection unit configured to receive at least one body signal from the sensor and detect a condition based on at least the body signal; and a therapy device configured to administer a therapy to at least one of a mucous membrane or a serous membrane of the patient. In another embodiment, the therapy device may an electrical stimulation unit configured to apply an electrical signal to a cranial nerve or a thermal therapy unit configured to cool a cranial nerve.

The at least one sensor configured to sense at least one body signal from a patient can be selected based on the condition to be detected, and the body signal or signals from which the detection is to be performed, among other parameters. Exemplary sensors are described in U.S. patent application Ser. No. 12/770,562, filed Apr. 29, 2010 and U.S. patent application Ser. No. 12/896,525, filed Oct. 1, 2010.

In one embodiment, the at least one sensor can be configured to receive at least one of a cardiac signal, a respiration signal (e.g., chest wall/abdominal motion or sound), a body movement signal, a skin resistance signal, a responsiveness signal, or an awareness signal. Alternatively or in addition, the at least one sensor can be configured to receive at least one of a blood oxygen saturation signal, an end-tidal $CO_2$, or lung sounds signal. Alternatively or in addition, the at least one sensor can be configured to receive at least one signal indicative of a body fluid (e.g., blood or saliva) concentration of a therapeutic medication.

The detection unit configured to receive at least one body signal from the sensor and detect a condition based on at least the body signal may, in one embodiment, be as described in U.S. patent application Ser. No. 12/770,562, filed Apr. 29, 2010, and U.S. patent application Ser. No. 12/896,525, filed Oct. 1, 2010. In one embodiment, the detection unit can be configured to detect a neurological condition, such as epilepsy, headache, or a movement disorder or a psychiatric condition, such as panic or anxiety attacks. Alternatively or in addition, the detection unit can be configured to detect a non-neurological condition, such as asthma, COPD, a cardiac disorder, vasodepressive syncope, or diabetes.

Sensor Smart fabrics and interactive textiles (SFIT) capable of sensing, actuating, generating/storing power and/or communicating may be used in this disclosure. Piezoelectric sensors and electrogoniometers may be also used to measure movement (e.g., breathing or joint flexion).

The therapy device administers the therapy, and can perform one or more additional tasks of identifying a need for therapy (responsive to the detection unit), and/or selecting a therapy (where multiple therapies are provided). The therapy device may be configured to receive an indication of a detected condition (e.g., from the detection unit) and administer the therapy to at least one of a mucous membrane or a serous membrane of the patient can comprise, in one embodiment, a reservoir containing a formulation of the therapy, a pump for delivery of the formulation, and a controller for controlling actions of the pump. The formulation may be administered as an aerosol, a gas, a liquid, or a controlled release gel to the mucous membrane or serous membrane. The therapy device can also comprise a power supply, a communication unit, and units capable of delivering additional therapies to locations other than a mucous membrane or a serous membrane (e.g., providing an electrical stimulation signal to a cranial nerve or a brain region).

In one embodiment, the medical device may further comprise a logging device configured to log one or more of the condition detected (e.g., an epileptic seizure), the date and time of detection, the severity (e.g., duration, intensity) of the condition, the type(s) of therapy(ies) delivered, the site(s) of delivery of the therapy(ies), the dose of the therapy(ies), the level of efficacy of the therapy(ies), the level of tolerance of the therapy(ies), and the presence or absence of adverse effects of the therapy(ies).

Each of the units of the system referred to above can be housed separately from one another, or any two or more can be housed together. Also, a component referred to as being part of one unit can be moved to another unit as a routine matter. Generally, any of the system units can be implanted in or permanently attached to the patient's body, reversibly coupled to the patient's body, configured for being worn, carried in a pocket, or otherwise borne on the outside of the patient's body, or located remotely from the patient. For example, the detection unit and can be located in a handheld, pocket-wearable, or comparably-sized and -shaped device. Such a device comprising the detection unit may be suitable for ambulatory use by the patient for determining a need for, and providing a therapy to, a mucous or serous membrane.

"Permanent attachment" can comprise surgical attachment or implantation, or less complicated techniques, similar to those used in piercing the skin or other tissues for adornment.

The therapy device can be an asthma inhaler or comparable device stored in proximity to the patient. Alternatively, the therapy device can be permanently attached or reversibly affixed to the patient's body.

In one embodiment, the therapy device can be configured for permanent attachment to an anatomical structure in proximity to at least one of the mucous membrane or the serous membrane. For example, the therapy device can be configured for attachment to the septum and/or the outer wall of the patient's nose, similar to the implantation of a nose ring through a piercing of the nose, with administration of the therapy being to a nasal mucous membrane.

In another embodiment, the therapy device may be configured for reversible coupling to an anatomical structure in proximity to at least one of the mucous membrane or the serous membrane. For example, an effect similar to a nose ring through a piercing can be achieved through use of one or more magnets, wherein a subunit external to the nose may be magnetically coupled to a subunit placed inside the nose, with a magnetic force between the subunits holding the total unit in place.

FIG. 1A provides a stylized diagram of a medical device system according to one embodiment of the disclosure. The depicted medical device system comprises a device 100, a sensor 212, and a delivery device 150 configured to deliver a therapy to a mucous membrane of the nose. Device 100 further includes a detection unit (not shown). The device 100 also contains a wireless communication unit for communication (175a) with the sensor 212 and with the delivery device 150. Communication (175b) between devices via wires is also contemplated in this disclosure.

The therapy device can be configured to deliver alternative (or additional) therapies to body structures other than a mucous membrane or a serous membrane. For example, in one embodiment, the therapy device can be configured to both administer a medication therapy to a mucous membrane of the nose of the patient, and deliver an electrical stimulation therapy to a trigeminal nerve of the patient.

Figure 1B:
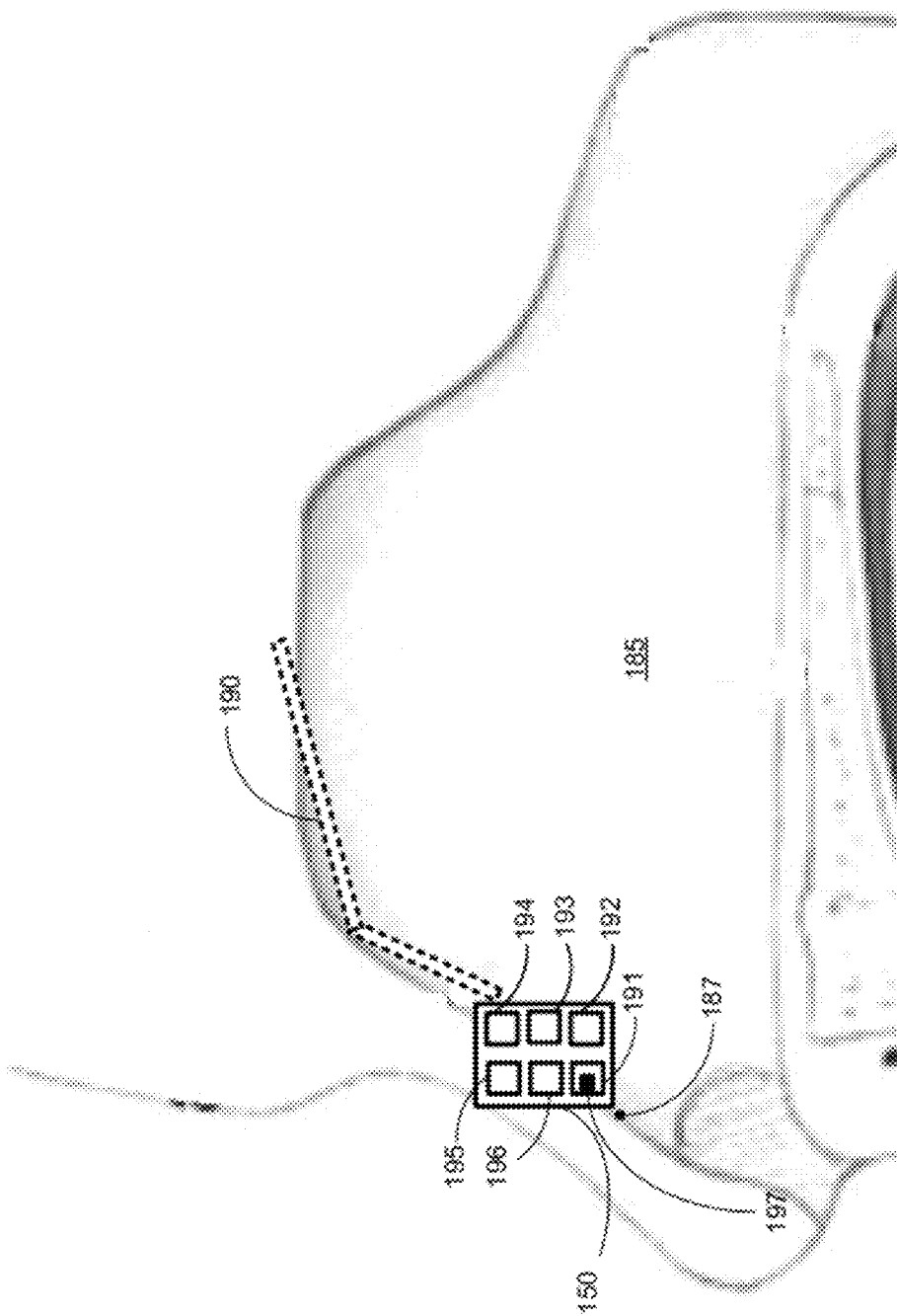
FIG. 1B provides a stylized diagram of a delivery device configured to deliver a therapy to a mucous membrane of the nose, to a cranial nerve, to a phrenic nerve, or two or more thereof, in accordance with one illustrative embodiment of the present disclosure.

FIG. 1B provides a stylized diagram of a delivery device 150 configured to deliver both a drug therapy to a mucous membrane 187 of the nasal cavity 185 and an electrical stimulation to a neural structure, such as an internal nasal branch of the anterior ethmoidal nerve 190 (a branch of the trigeminal nerve). In one embodiment, the delivery device 150 comprises a pump 191 and a reservoir 192, for delivery of a medication to the mucous membrane 187. The pump 191 may include a nozzle for delivery of medication. In another embodiment, the nozzle 197 may be external to the pump 191. In another embodiment, the pump 191 may be an actuator capable of moving medication from the delivery device 150 to the mucous membrane 187. In an alternative embodiment, pump 191 may be coupled to a gas flow tube (e.g., an oxygen tube, not shown) capable of entraining the medication delivered by pump 191.

The delivery device 150 may also include a reservoir 192 from which medication may be dispensed via a port without use of a pump; for example, the medicament may be stored at a certain pressure so that its release may be manually or automatically controlled by a valve. The medicament may be dispersed in a propellant such as oxygen, heliox, carbon dioxide, a hydrofluoroalkane or chlorofluorocarbon or the like; this delivery modality may be also applicable to highly volatile compounds. The delivery device may be one of a metered dose inhaler, dry powder inhaler, small or large volume nebulizer (e.g., jet, mesh, ultrasonic). In another embodiment, the delivery device 150 may also comprise an electrical stimulator 194, for delivery of electrical stimulation to a cranial nerve (e.g., anterior ethmoidal nerve of the trigeminal nerve) 190. In another embodiment the electrical stimulator 194 may be replaced by a thermal (e.g. cooling or heating) unit or a second drug delivery unit. The delivery device 150 may also comprise one or more of a controller 193, a communication unit 195, and a power supply 196. In alternative embodiments, these units may be subunits of device 100 (FIG. 1A).

Referring again to FIG. 1B, in one embodiment, the power supply 196 may be a standalone power source. In another embodiment, the power supply 196 may include a power source capable of being charged via an external source, e.g., light source, radio frequency (RF) source, inductive coupling, and/or the like. In some embodiments, the delivery device 150 can be configured to receive power from the device 100. In such embodiments, the delivery device 150 may not require a power supply 196, but instead may receiving power from an external source.

Figure 2A:
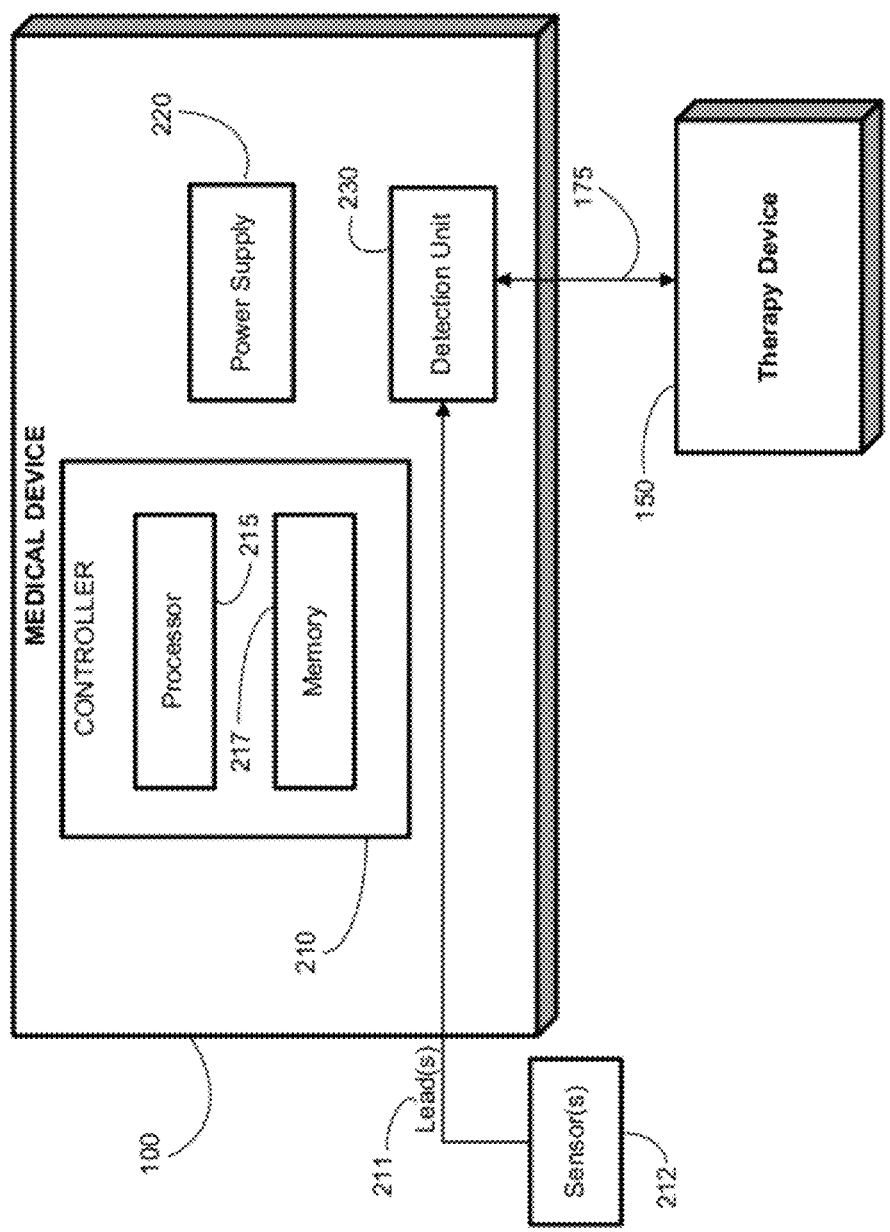
FIG. 2 provides a block diagram of a medical device system that includes a medical device and a therapy device, in accordance with one illustrative embodiment of the present disclosure.

Turning now to FIG. 2A, a block diagram depiction of a medical device 100 is provided, in accordance with one illustrative embodiment of the present disclosure. In some embodiments, the medical device 100 may be implantable, while in other embodiments the medical device 100 may be completely external to the body of the patient (as shown in FIG. 1A) or partly implanted and partly external.

Medical device 100 may comprise a controller 210 capable of controlling various aspects of the operation of the medical device 100. The controller 210 may be capable of receiving internal data or external data, and in one embodiment, may be capable of causing a therapy device 150 to deliver a therapy to one or more mucous or serous membranes of the patient's body for treating a medical condition or controlling the body concentration of a medication. Generally, the controller 210 may be capable of affecting substantially all functions of the medical device 100.

The controller 210 may comprise various components, such as a processor 215, a memory 217, etc. The processor 215 may comprise one or more microcontrollers, microprocessors, etc., capable of performing various executions of software components. The memory 217 may comprise various memory portions where a number of types of data (e.g., internal data, external data instructions, software codes, status data, diagnostic data, etc.) may be stored. The memory 217 may comprise one or more of random access memory (RAM), dynamic random access memory (DRAM), electrically erasable programmable read-only memory (EEPROM), flash memory, etc.

The medical device 100 may also comprise a power supply 220. The power supply 220 may comprise a battery, voltage regulators, capacitors, etc., to provide power for the operation of the medical device 100. Power supply 220 comprises a power source that in some embodiments may be rechargeable. In other embodiments, a non-rechargeable power source may be used. Power supply 230 may comprise a lithium/thionyl chloride cell or a lithium/carbon monofluoride (LiCFx) cell if the medical device 100 is implantable, or may comprise conventional watch or 9V batteries for external (i.e., non-implantable) embodiments. Other battery types may also be used.

The medical device system depicted in FIG. 2 may also comprise one or more sensor(s) 212. In the depicted embodiment, the sensor(s) 212 are coupled via sensor lead(s) 211 to the medical device 100. In other embodiments, the sensor(s) 212 can be in wireless communication with the medical device 100. Sensor(s) 212 are capable of receiving signals related to a body parameter, such as the patient's heart activity, blood pressure, and/or temperature, among others, and delivering the signals to the medical device 100. The sensor 212 may also be capable of detecting kinetic signal associated with a patient's movement. The sensor 212, in one embodiment, may be an accelerometer. The sensor 212, in another embodiment, may be an inclinometer. In another embodiment, the sensor 212 may be an actigraph or a gyroscope. In one embodiment, the sensor(s) 212 may be implanted in the patient's body. In other embodiments, the sensor(s) 212 are external structures that may be placed on the patient's skin, such as over the patient's heart or elsewhere on the patient's torso or limbs. The sensor 212, in one embodiment, may be a multimodal signal sensor capable of detecting various body signals, including cardiac signals associated with the patient's cardiac activity and kinetic signals associated with the patient's movement.

The detection unit 230 may be capable of detecting one or more conditions (e.g., an epileptic seizure, blood oxygen levels, or an unacceptably high or low blood glucose level) based upon one or more signal(s) provided by the sensor(s) 212. The detection unit 230 may comprise software module(s) that are capable of performing various interface functions, filtering functions, etc. In another embodiment, the detection unit 230 may comprise hardware circuitry that may be capable of performing these functions. In yet another embodiment, the detection unit 230 may comprise hardware, firmware, software and/or any combination thereof. Detection unit 230 may be capable of analyzing the signals from sensors 212 and detecting the presence of a condition based on the signals. In one embodiment, the detection unit comprises executable logic for detecting an epileptic seizure from heart beat data from heart sensing electrodes and/or body motion data from an accelerometer.

The system depicted in FIG. 2A also includes a therapy device 150, which may be in (wired or wireless) communication 175 with the medical device 100. The therapy device 150 can then administer a desired therapy to a mucous membrane, a serous membrane, or directly or indirectly to a cranial nerve of the patient. In alternative embodiments, therapy device 150 may be included as part of medical device 100.

Figure 2B:
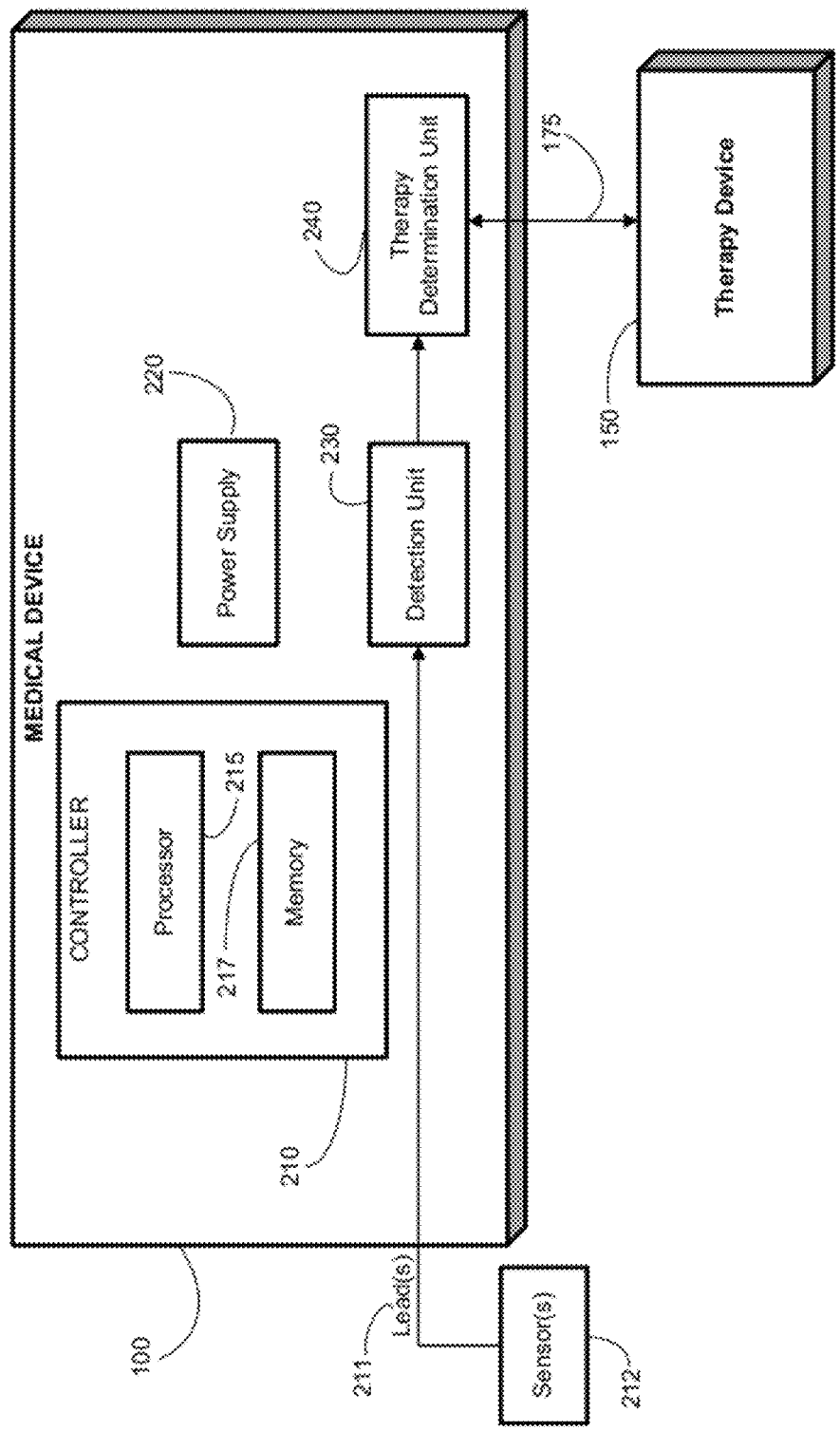

FIG. 2B presents an alternative embodiment of medical device 100. In this embodiment, the medical device system further comprises a therapy determination unit 240. The therapy determination unit 240 may be configured to receive an indication of a detected condition from the detection unit and to determine at least one therapy for the condition based on the detected condition. A therapy determination unit 240 may be useful for inclusion in a medical device system for which it would be desirable to select one or more of multiple therapies during operation of the medical device system. In some embodiments, the therapy determination unit 240 may be provided with information to determine any of a number of possible therapies to treat the detected condition. In one embodiment, the therapy can be a medication in one or more particular formulations and doses; an electrical stimulation, such as of a cranial nerve; or both.

The therapy determination unit 240 may be capable of selecting a therapy and controlling its dose, mode and rate of delivery, based on a detection of a condition by the detection unit 230. In alternative embodiments, therapy determination unit 240 may simply initiate a predetermined therapy. Therapy determination unit 240 may comprise software module(s) that are capable of performing various interface functions, filtering functions, etc. In another embodiment, therapy determination unit 240 may comprise hardware circuitry to perform these functions. More generally, therapy determination unit 240 may comprise hardware, firmware, software and/or any combination thereof. The therapy determination unit 240 may be shown in more detail in FIG. 3 and accompanying description below.

In some embodiments, the medical device 100 may further comprise a logging unit 250. The logging unit 250 may be capable of at least one of logging one or more of the condition detected (e.g., an epileptic seizure) by the detection unit 230, the date and time of detection, the severity (e.g., duration, intensity) of the condition, the type(s) of therapy(ies) delivered, the sites) of delivery of the therapy(ies), the dose of the therapy(ies) the level of efficacy of the therapy(ies), the level of tolerance of the therapy(ies) the presence or absence of adverse effects of the therapy(ies).

It should be borne in mind the logging unit 250 is optional, and need not be present in every embodiment in accordance with the present disclosure.

One or more of the blocks illustrated in the block diagram of the medical device 100 in FIGS. 2A-2B may comprise hardware units, software units, firmware units, or any combination thereof. Additionally, one or more blocks illustrated in FIGS. 2A-2B may be combined with other blocks, which may represent circuit hardware units, software algorithms, etc. Additionally, any number of the circuitry or software units associated with the various blocks illustrated in FIGS. 2A-2B may be combined into a programmable device, such as a field programmable gate array, an ASIC device, etc.

Figure 3:
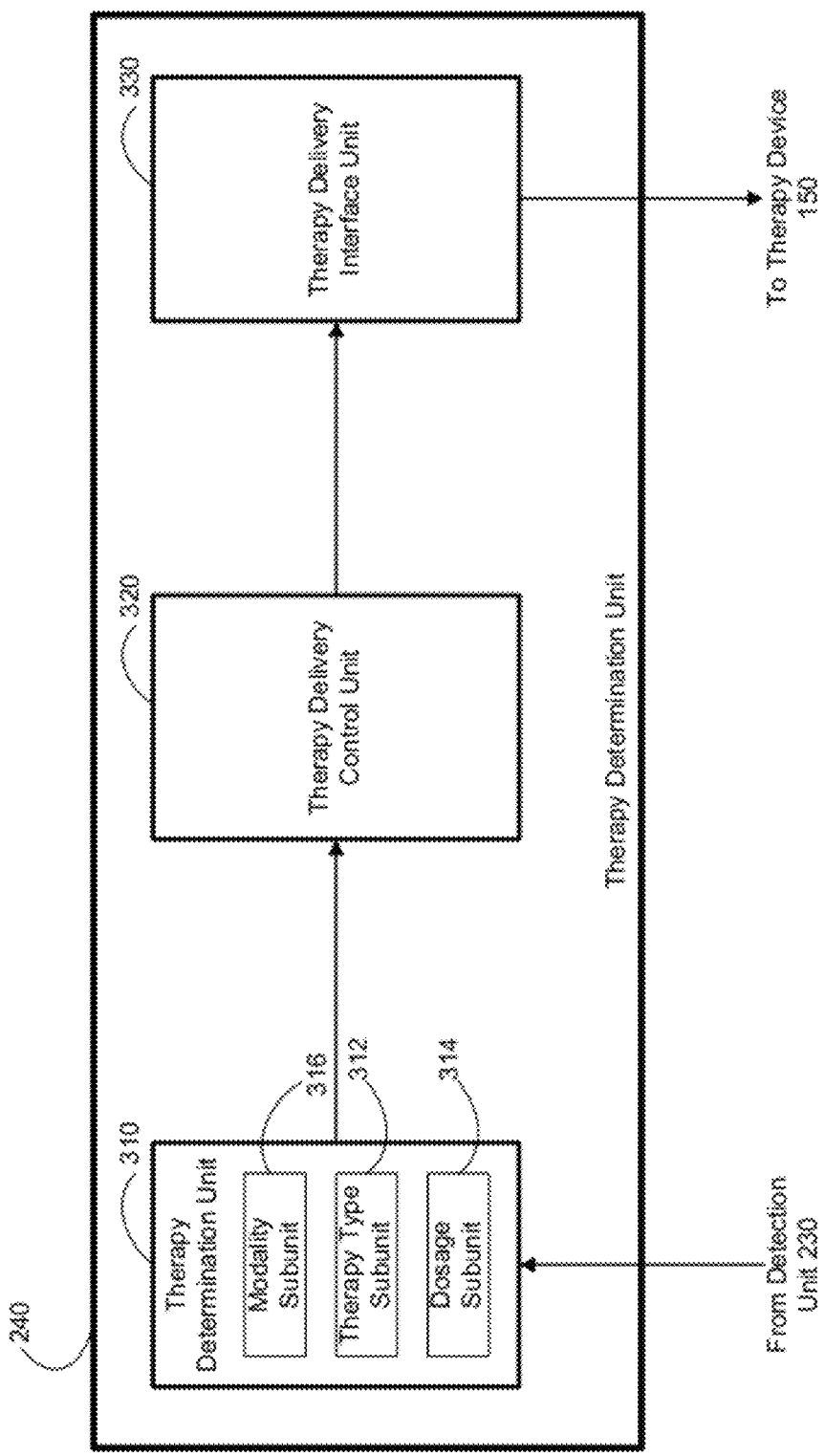
FIG. 3 provides a block diagram of a mucous or serous membrane therapy unit, in accordance with one illustrative embodiment of the present disclosure.

FIG. 3 provides a block diagram of an embodiment of a therapy determination unit 240. Upon receipt from the detection unit 230 of a signal indicating a detection of a condition (e.g., an epileptic seizure or an undesirable medicament concentration), a therapy determination unit 310 determines which modality of administration (e.g., pharmacological, electrical, thermal, etc.). should be used, in modality subunit 316; which type of therapy (e.g., which of various possibilities within a particular modality, e.g., which medications or formulations of a single medication or combination of medications of the pharmacological modality) should be administered, to which site(s) it should be delivered, in therapy type subunit 312; what dosage of the therapy should be administered, at what rate, and whether delivered continuously or in pulses in dosage subunit 314. Modality subunit 316 may select one or more of a pharmacologic, electrical, thermal, biofeedback or cognitive therapy as well as the delivery target (e.g., one or more mucous and/or serous membranes; and/or a cranial nerve).

The determinations made by the therapy determination unit 310 are then communicated to a therapy delivery control unit 320. The therapy delivery control unit 320 prepares an instruction to the therapy device 150, and the instruction may be communicated to the therapy device 150 by the therapy delivery interface unit 330.

In some embodiments, the therapy delivery interface unit 330 can also receive indications from the therapy device 150 as to whether the therapy device 150 is fully functioning, partially functioning (e.g., the therapy device 150 may have depleted its supply of one medication or formulation and thus be unable to administer that medication or formulation), or not functioning. The therapy deliver interface unit 330 may, in some embodiments, communicate indications regarding the functionality of the therapy device 150 to other units of the therapy determination unit 240, or other units of the medical device 100, or other components of the system. Such indications may, for example, lead the therapy determination unit 310 to determine an alternative therapy; or alert the patient, the physician, or a caregiver regarding an impaired functionality of the therapy device 150; among others.

Figure 4:
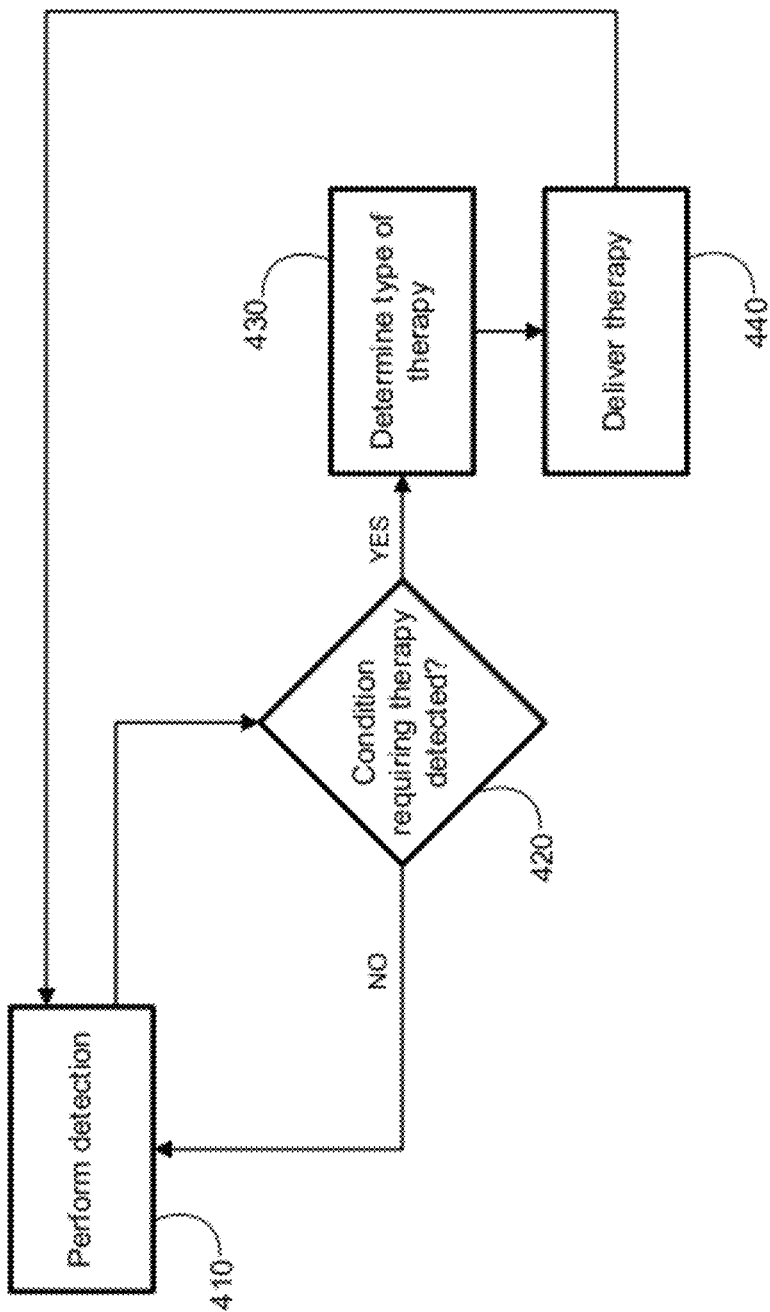
FIG. 4 shows a flowchart of an implementation of a method, in accordance with one illustrative embodiment of the present disclosure.

FIG. 4 shows a flowchart of an implementation of a therapy delivery method. A detection of a physiological event may be performed at 410. The event detected at 410 may or may be a condition requiring therapy. If a determination is made at 420 that a condition requiring therapy was not detected, flow returns to collect and analyze body signal(s) as needed to perform detection at 410. A delay may be introduced prior to performing a detection at 410, in order to reduce computational effort, power consumption, and signals bandwidth consumption below the levels that would obtain if detection were performed 410 on a continuous basis. In some embodiments the delay may be implemented by performing batch analysis of the signals from sensors 212 in the detection unit 230. For example, processor 215 may update the detection algorithm in detection unit 230 at intervals, such as every 5 seconds, every 2 or more heart beats, only upon an accelerometer reaching a threshold level, etc.

The performing at 410 is shown in more detail in FIG. 5 and discussed below.

At 420, determining whether the event detection requires therapy may involve characterization of the event. For example, the characterization can include a finding of what particular condition the patient is suffering, its severity, and/or its location in the body, among other findings. More information regarding determination of severity and location in the body of epileptic events can be found in U.S. patent application Ser. No. 13/040,996, filed Mar. 4, 2011 and U.S. patent application Ser. No. 13/091,033, filed Apr. 20, 2011, both of which are hereby incorporated herein by reference in their entirety.

If a condition requiring therapy is detected at 420, the type of therapy (as well as its target, modality, dosage, rate, etc., not shown) may be determined at 430. One embodiment of the determining at 430 is shown in more detail in FIG. 6 and discussed below. In some embodiments the therapy determination at 430 may be omitted and a predetermined therapy may be delivered at 440 to at least one of a mucous membrane or serous membrane of the patient. Flow then returns to the perform detection at 410, optionally with any desired delay (not shown).

Figure 5:
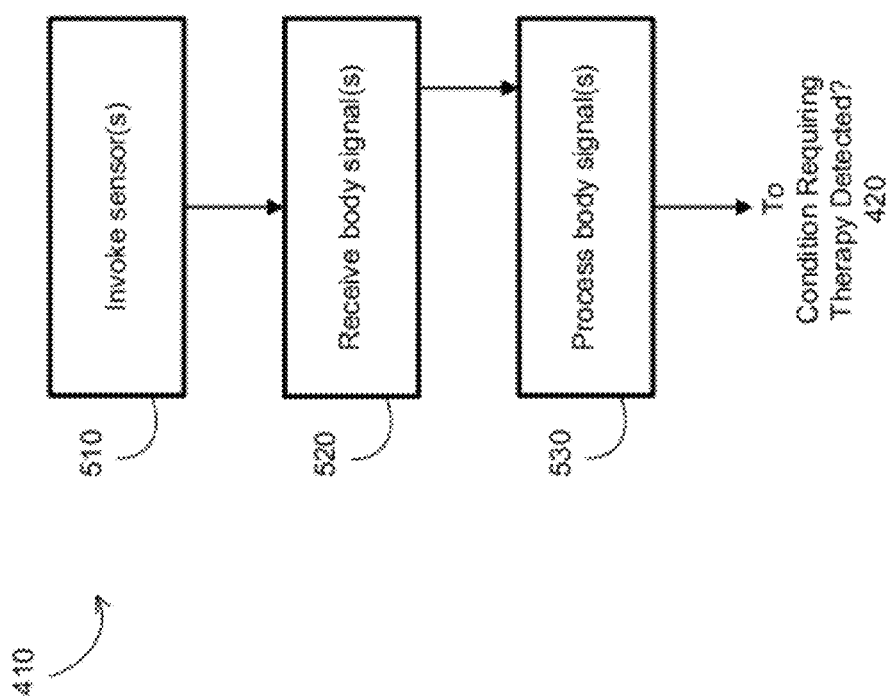
FIG. 5 shows a flowchart of an implementation of a detection of the method shown in FIG. 4, in accordance with one illustrative embodiment of the present disclosure.

FIG. 5 shows a flowchart of an implementation of the detection performed at 410 of the method shown in FIG. 4. At 510, the invocation of the sensor(s) may be used to collect the one or more body signals on which the detection may be based. As should be apparent, in some embodiments, the sensor(s) are always acquiring data from the patient's body, and the invocation at 510 indicates an operation whereby the data may be actively considered elsewhere in the method.

After the sensor(s) are invoked at 510, body signal(s) are received at 520. The body signal(s) may be processed at 530 using signal processing techniques to render them more suitable for use elsewhere in the method. After processing the body signals, a determination may be made at 420, as shown in FIG. 4, regarding whether the body signal(s) indicate the onset of a condition.

Figure 6:
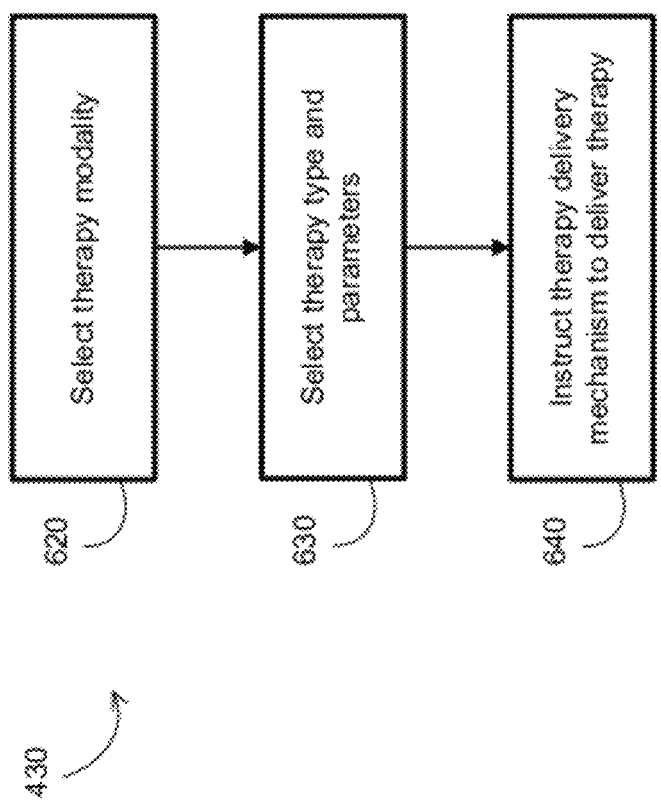
FIG. 6 shows a flowchart of an implementation of a therapy determination of the method shown in FIG. 4, in accordance with one illustrative embodiment of the present disclosure.

FIG. 6 shows a flowchart of an implementation of one embodiment of a therapy determination made at 430 of the method shown in FIG. 4. As should be apparent from the above discussion, in other embodiments, when there is only one therapy predetermined prior to implementation of the method, the therapy determination at 430 may be notional.

A selection at 620 may be made of the therapy modality to be used. The selection may be from one or more therapy modalities (e.g., pharmacological, electrical, thermal, etc.). The selection at 620 may also find that one or more therapy modalities is unavailable, e.g., a therapy device 150 may be malfunctioning or may be depleted of one or more medications or formulations thereof, among other possibilities.

In light of the selection at 620 of the therapy modality, a therapy type and its parameters can be selected at 630. For example, the selection at 630 may be of one or more of multiple drugs provided as part of a pharmacological modality, with further selection of one or more of a dosage, a route of administration, etc. Upon selection at 630 of the therapy type and parameters mechanism, the therapy delivery mechanism can be instructed at 640 to deliver the therapy.

Figure 7:
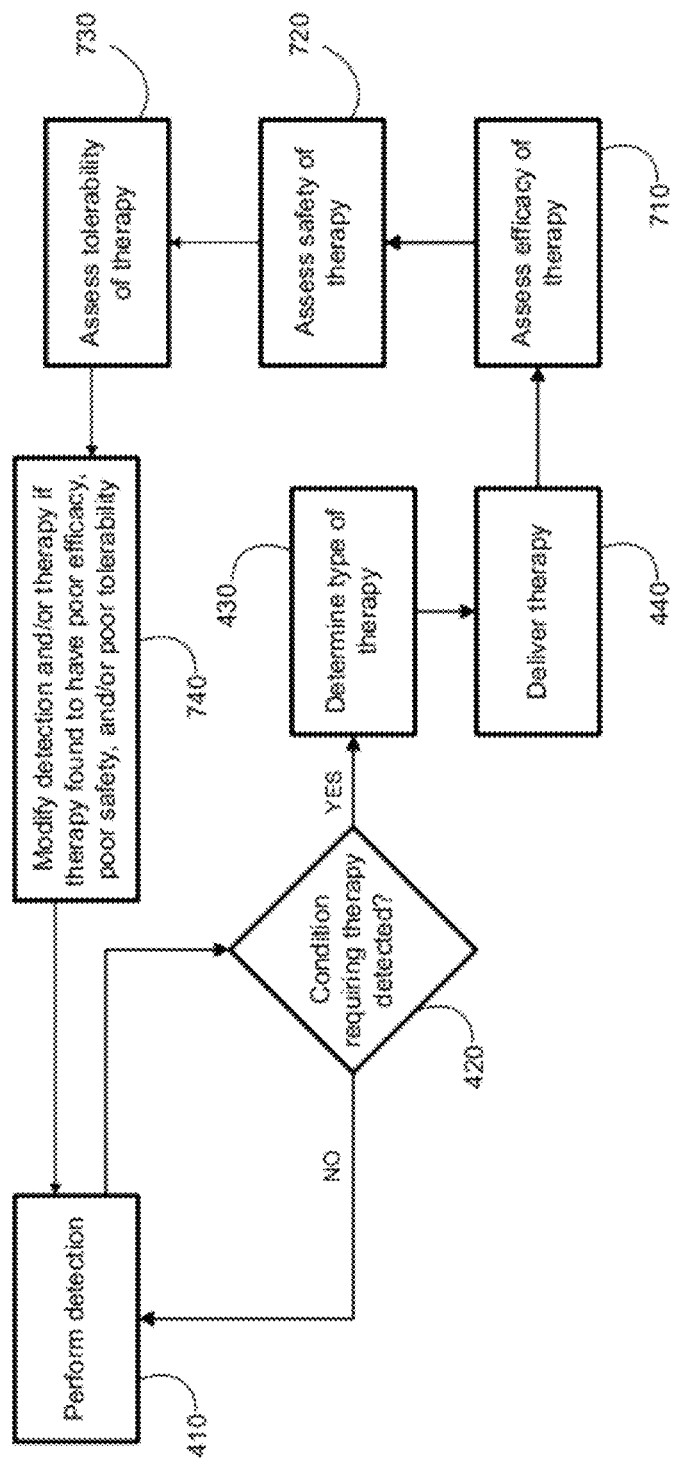
FIG. 7 shows a flowchart of an implementation of a method, in accordance with one illustrative embodiment of the present disclosure.

FIG. 7 shows a flowchart of an alternative implementation of a therapy delivery method. The method of FIG. 7 has some common flow diagram elements with the method shown in FIG. 4. Like reference numerals in FIG. 7 have been described above regarding FIG. 4. In addition to the flow diagram elements of FIG. 4, the implementation of FIG. 7 may provide an assessment of the efficacy, safety, and/or tolerability of the therapy. After the therapy is delivered at 440, the efficacy of the therapy may be assessed at 710 by the same or similar techniques to those used to detect of the condition at 410, e.g., by analyzing body signals to determine if the condition persists after the therapy. For example, if the event detected at 410 was an epileptic seizure based on an elevation in heart rate above baseline and a pattern of body movement consonant with a seizure, the efficacy of the therapy can be assessed at 710 from the patient's heart rate and body movements after delivery of the therapy.

A safety of the therapy may be assessed at 720. Safety of therapy may be assessed at 720 by techniques comparable to the assessment of efficacy at 710. For example, the detection at 410 and assessment of efficacy at 710 may be based on heart rate and body movement signals, and a depression of heart rate to a level significantly below baseline can be considered an indication of a lack of safety (or the presence of an adverse event). Safety of therapy may also be assessed at 720 by other techniques. For example, if a medication has a blood concentration ceiling, beyond which the blood concentration of the signal is considered unsafe, the blood concentration of the medication can be measured as part or all of the assessment at 720 of safety.

A tolerability of the therapy can also be assessed at 730. For example, an input can be received from the patient indicating whether the therapy is tolerable, or indicating the level of tolerability on a particular scale. For another example, autonomic signals indicative of the patient's level of perceived pain can be analyzed to determine a tolerability of the therapy. It should be borne in mind that the autonomic signals are objective and unless the patient has been successfully trained in bio-feedback techniques, are not consciously controllable by the patient, in contrast to a patient's subjective awareness of his pain and his controllable communication regarding it.

As part of one or more of the assessments at 710-730, a number of parameters of the condition and/or the therapy can be logged. Such parameters include, but are not limited to, time of detection of condition, severity of condition, type of therapy chosen, therapy dose, therapy rate, therapy delivery target, efficacy, safety, and tolerability, among others.

After assessing efficacy at 710, assessing safety at 720, and/or assessing tolerability at 730, and prior to returning to performing detection at 410, one or more of the detection at 410 and the therapy determination at 430 can be modified at 740 to improve efficacy, safety, and/or tolerability. For an example of a modification at 740 of detection at 410, if the therapy is found to have poor tolerability, detections can be made more stringent, allowing less severe conditions to go untreated in future iterations of the process in order to spare the patient side effects of treatment. For an example of a modification at 740 of therapy determination at 430, if the therapy is found to have poor efficacy, an alternative therapy can be determined in future iterations of the process. In the case of a drug concentration above a therapeutic, tolerable or safe level, if a condition is detected, a different drug or modality may be delivered.

INCORPORATION BY REFERENCE

The following United States patents and patent applications are specifically incorporated herein by reference in their entirety.

U.S. patent application Ser. No. 12/770,562, filed Apr. 29, 2010

U.S. patent application Ser. No. 12/896,525, filed Oct. 1, 2010

U.S. patent application Ser. No. 13/040,996, filed Mar. 4, 2011

U.S. patent application Ser. No. 13/091,033, filed Apr. 20, 2011

What is claimed is:

1. A method, comprising:
   receiving at least one body signal from a patient, wherein said body signal is at least one of a cardiac signal, a respiration signal, a body movement signal, a skin resistance signal, a responsiveness signal, or an awareness signal;
   detecting epilepsy of said patient based on said body signal;
   administering a therapy for said epilepsy to a nasal mucous membrane of said patient, in response to said detecting; and
   delivering an electrical stimulation therapy to a cranial nerve of said patient.

2. A method, comprising:
   receiving at least one skin resistance signal from a patient;
   detecting migraine of said patient based on said skin resistance signal; and
   administering a therapy for said migraine to a nasal mucous membrane of said patient, in response to said detecting.

3. A method, comprising:
   receiving at least one signal indicative of a concentration of a therapeutic medication in a body fluid from a patient;
   detecting said concentration of said therapeutic medication being below a first concentration or above a second concentration; and
   (i) administering a supplemental dosage of said therapeutic medication sufficient to raise said blood concentration of said therapeutic medication above said first concentration to a nasal mucous membrane of said patient, in response to said detecting said concentration being below said first concentration; or (ii) at least one of reducing the dose of said therapeutic medication, reducing the rate of delivery of said therapeutic medication, or delaying the delivery of said therapeutic medication, in response to said detecting said concentration being above said second concentration.

4. The method of claim 3, wherein said therapy is a medicament, said medicament is selected from a benzodiazepine, a barbiturate, a CNS depressant drug, an anti-seizure drug, a local anesthetic, a vasoactive agent, an anti-inflammatory drug, a non-narcotic analgesic, a narcotic analgesic, a medicinal gas, or two or more thereof, wherein the medicament is delivered in an absorbable or inhalable form.

5. A medical device system, comprising:
   at least one sensor configured to sense at least one of a cardiac signal, a body movement signal, a skin resistance signal, a responsiveness signal, or an awareness signal from a patient;
   a detection unit configured to receive said at least one signal from said sensor and detect a condition based on at least said signal, wherein said condition is epilepsy; and
   a therapy device configured to receive an indication of a detected condition from said detection unit and administer a therapy for said detected condition to at least one of a mucous membrane or a serous membrane of said patient,
   wherein (i) said therapy device is configured for permanent attachment to an anatomical structure in proximity to at least one of said mucous membrane or said serous membrane, (ii) said therapy device is configured to administer said therapy to a mucous membrane of the nose of said patient, and said therapy device is further configured to deliver an electrical stimulation therapy to a cranial nerve of said patient, or (iii) both.

6. A medical device system, comprising:
- at least one sensor configured to sense at least one of a cardiac signal, a body movement signal, a skin resistance signal, a responsiveness signal, or an awareness signal from a patient;
- a detection unit configured to receive said at least one signal from said sensor and detect a condition based on at least said signal, wherein said condition is epilepsy;
- a therapy device configured to receive an indication of a detected condition from said detection unit and administer a therapy for said detected condition to at least one of a mucous membrane or a serous membrane of said patient; and
- a logging device configured to log one or more of the condition detected, the date and time of detection, the severity of the condition, the type(s) of therapy(ies) delivered, the site(s) of delivery of the therapy(ies), the dose of the therapy(ies), the level of efficacy of the therapy(ies), the level of tolerance of the therapy(ies), and the presence or absence of adverse effects of the therapy(ies).

7. A computer-readable storage device for storing instructions that, when executed by a processor, perform a method, comprising:
- detecting epilepsy requiring a therapy, based on at least one body signal sensed from a patient;
- delivering a therapy for said condition to a nasal mucous membrane of said patient; and
- delivering an electrical stimulation therapy to a cranial nerve of said patient.

8. The non-transitory computer readable program storage unit of claim 7, wherein the at least one body signal is selected from a cardiac signal, a body movement signal, a skin resistance signal, a responsiveness signal, and an awareness signal.

* * * * *